US012807986B2

(12) United States Patent
Huang et al.

(10) Patent No.: US 12,807,986 B2
(45) Date of Patent: Nov. 24, 2026

(54) NUCLEIC ACID AMPLIFICATION IN-SITU REAL-TIME DETECTION SYSTEM AND METHOD USING MICROFLUIDIC CHIP THROUGH OPTICAL FIBER SENSING

(71) Applicant: TSINGHUA UNIVERSITY, Beijing (CN)

(72) Inventors: Guoliang Huang, Beijing (CN); Xiangyu Ji, Beijing (CN); Rongxin Fu, Beijing (CN); Qin Huang, Beijing (CN); Wenli Du, Beijing (CN); Li Ma, Beijing (CN); Xianbo Luo, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 1243 days.

(21) Appl. No.: 17/765,996

(22) PCT Filed: Nov. 2, 2020

(86) PCT No.: PCT/CN2020/125797

§ 371 (c)(1),
(2) Date: Apr. 1, 2022

(87) PCT Pub. No.: WO2021/093622

PCT Pub. Date: May 20, 2021

(65) Prior Publication Data

US 2022/0340960 A1 Oct. 27, 2022

(30) Foreign Application Priority Data

Nov. 14, 2019 (CN) .......................... 201911111985.4

(51) Int. Cl.

*B01L 7/00* (2006.01)
*B01L 3/00* (2006.01)

(Continued)

(52) U.S. Cl.

CPC ...... *C12Q 1/6844* (2013.01); *B01L 3/502715* (2013.01); *B01L 7/52* (2013.01);

(Continued)

(58) Field of Classification Search

CPC .. B01L 3/502715; B01L 7/52; B01L 2200/10; B01L 2200/147; B01L 2200/16;

(Continued)

(56) References Cited

FOREIGN PATENT DOCUMENTS

| | | | | |
|---|---|---|---|---|
| CN | 106085842 A | * | 11/2016 | ............ B01L 3/5027 |
| CN | 108913599 A | * | 11/2018 | ............ C12M 41/48 |

OTHER PUBLICATIONS

International Search Report issued in corresponding International Application No. PCT/CN2020/125797; mailed Jan. 25, 2021; 6 pgs.

(Continued)

*Primary Examiner* — Lydia Edwards

(74) *Attorney, Agent, or Firm* — HAUPTMAN HAM, LLP

(57) ABSTRACT

A nucleic acid amplification in-situ real-time detection system and method using a micro-fluidic chip through optical fiber sensing. The system includes a white light source, a detection optical path, a microfluidic chip and a spectrum acquisition, processing and display module, which are connected in sequence. The detection optical path is configured to transmit white light from the white light source to the micro-fluidic chip and transmit an optical signal made by the microfluidic chip to the spectrum acquisition, processing and display module. The micro-fluidic chip is configured to carry out biochemical reaction; the spectrum acquisition, processing and display module is configured to acquire the optical signal, analyze the signal and generate a visual biochemical reaction real-time dynamic-change signal curve. This microfluidic chip real-time detection device detects nucleic acid amplification information by using a (Continued)

white light interfered hyperspectral method, so fluorescence-labeled analyte and non-fluorescence-labeled analyte are detected.

8 Claims, 2 Drawing Sheets

(51) Int. Cl.

| | |
|---|---|
| ***B01L 99/00*** | (2010.01) |
| ***C12Q 1/6844*** | (2018.01) |
| ***G01N 21/64*** | (2006.01) |
| ***G01N 33/58*** | (2006.01) |
| *C12Q 1/6841* | (2018.01) |

(52) U.S. Cl.
CPC ... *B01L 2200/16* (2013.01); *B01L 2300/0654* (2013.01); *B01L 2300/0819* (2013.01); *B01L 2300/18* (2013.01); *C12Q 1/6841* (2013.01)

(58) Field of Classification Search
CPC ..... B01L 2300/0654; B01L 2300/0803; B01L 2300/0819; B01L 2300/18; B01L 2300/1838; B01L 2400/0409; G01N 2021/6439; G01N 2021/7779; G01N 21/0332; G01N 21/07; G01N 21/6428; G01N 21/65; G01N 21/77; G01N 2201/0231; G01N 2201/08; C12Q 1/6841; C12Q 1/6844; C12Q 2543/101; C12Q 2561/113; C12Q 2563/107; C12Q 2565/607; C12Q 2565/629
See application file for complete search history.

(56) References Cited

OTHER PUBLICATIONS

First Office Action issued in corresponding Chinese Application No. 201911111985.4; mailed Feb. 2, 2021; 7 pgs.

* cited by examiner

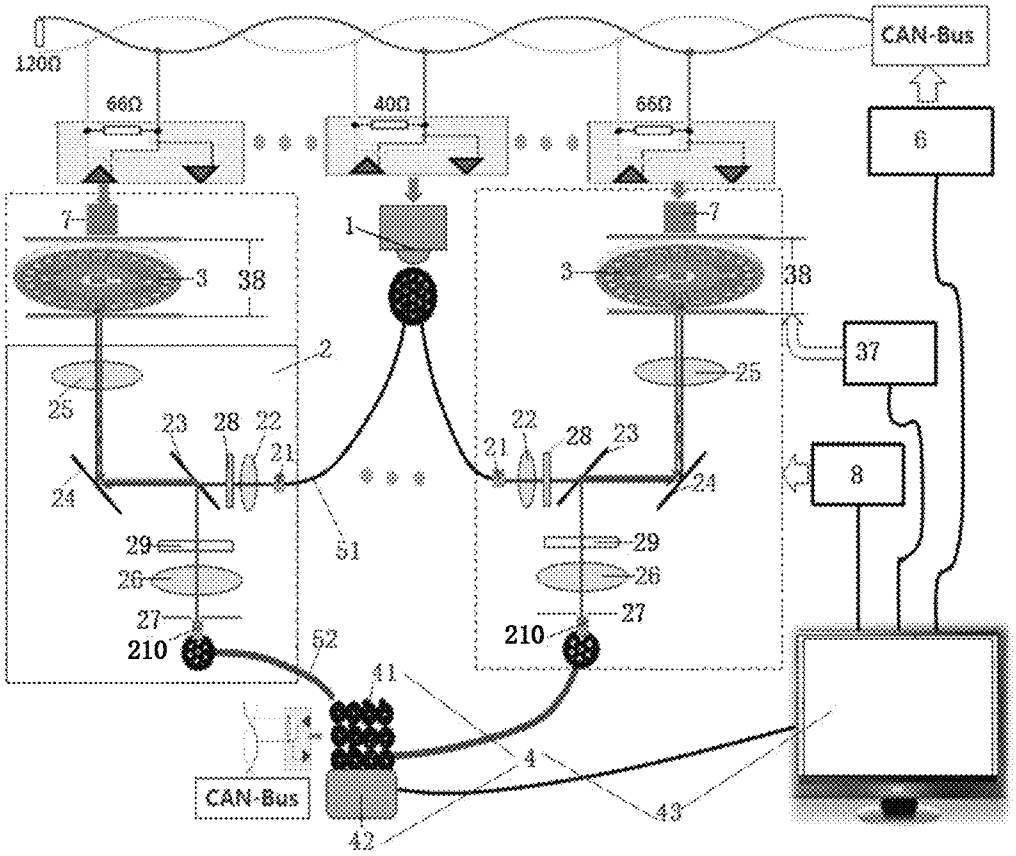
Fig. 1
Fig. 2(A)
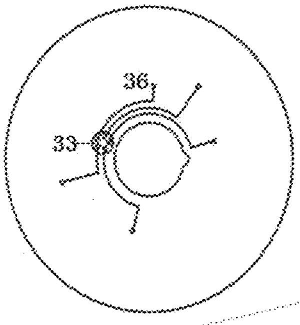
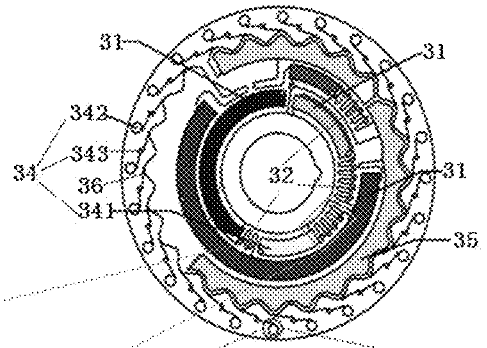
Fig. 2(B)
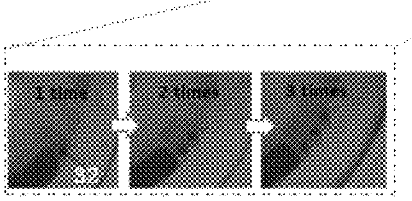
Fig. 2(C)
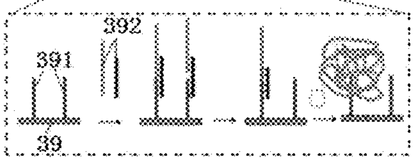
Fig. 2(D)

Fig. 3(A)
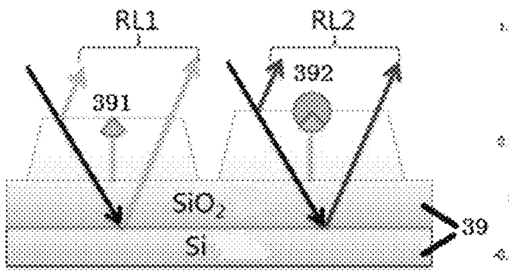
Fig. 3(B)
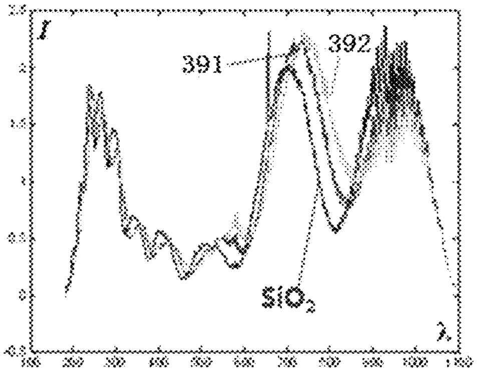
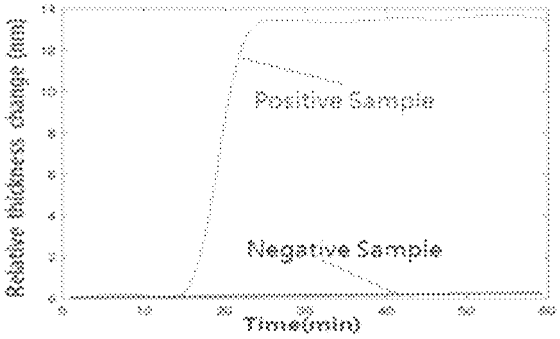
Fig. 3(C)
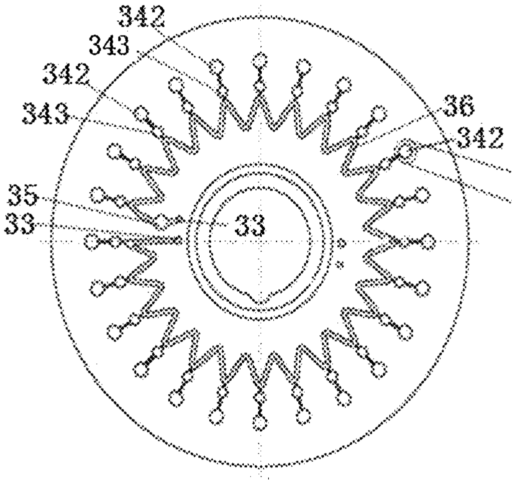
Fig. 4(A)
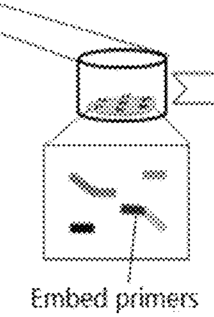
Fig. 4(B)
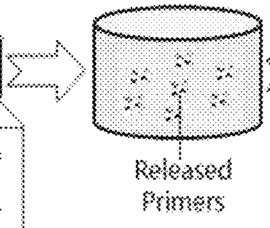
Fig. 4(B)
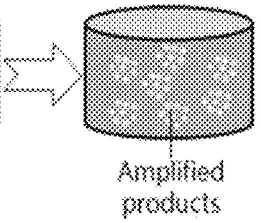
Fig. 4(D)

NUCLEIC ACID AMPLIFICATION IN-SITU REAL-TIME DETECTION SYSTEM AND METHOD USING MICROFLUIDIC CHIP THROUGH OPTICAL FIBER SENSING

RELATED APPLICATIONS

The present application is a U.S. National Phase of International Application Number PCT/CN2020/125797 filed Nov. 2, 2020, and claims priority to Chinese Application Number 201911111985.4 filed Nov. 14, 2019.

FIELD OF THE INVENTION

The present disclosure relates to a nucleic acid amplification in-situ real-time detection system and method using a microfluidic chip through optical fiber sensing, which belong to the technical field of biological detection.

BACKGROUND OF THE INVENTION

Nucleic acid amplification is an advanced biomedical analysis technology in the 20th century, by which a specific sequence of nucleic acid fragments can be amplified to $10^9$ copy numbers within 120 minutes, and high sensitivity molecular diagnosis is enabled thereby. The Nucleic acid amplification technology mainly includes two major categories, i.e., temperature-varying amplification and isothermal amplification.

As a representation for the temperature-varying amplification, Polymerase Chain Reaction (PCR) is the earliest nucleic acid amplification technology, in which nucleic acid amplification reaction is initiated by fully matching two positive and negative specific primers, and a period of each amplification cycle is about 90 seconds, including three stages of denaturation, annealing and extension. The denaturation requires a high temperature of 94° C. for 15 seconds, the annealing is performed at a low temperature of 60° C. for 30 seconds, and the extension is performed at 72° C. by using the primers as a starting point of nucleic acid synthesis to enable extension along a direction of a template for 45 seconds under the action of enzymes. PCR amplification is implemented by keeping a continuous loop with dozens of amplification cycles. In the temperature-varying amplification method, nucleic acid synthesis and amplification can be performed only in the phase of extension in every amplification cycle, while the phases of denaturation and annealing are only used as preparation for nucleic acid amplification. Therefore, the effective duration of temperature-varying amplification is less than 50% of the total time.

In order to improve the efficiency of nucleic acid amplification, isothermal amplification technologies have been invented, for example, the Strand Displacement Amplification (SDA) technology reported by Walker GT in 1992, the Rolling Circle Amplification (RCA) technology reported by Liu D in 1996, the Loop-mediated Isothermal Amplification (LAMP) technology reported by TsugunoriNotomi in 2000, and Recombinase Polymerase Amplification (RPA) reported by Lutz Sascha in 2010, etc. Isothermal amplification is kept at a fixed temperature throughout the entire process without high-temperature denaturation or low-temperature annealing. The amplification has a very fast speed so that target nucleic acid can be replicated up to $10^9$~$10^{10}$ copy numbers within a short time. The isothermal amplification reaches a time utilization of 100% and thus has the higher nucleic acid amplification efficiency.

No matter it is the temperature-varying amplification or the isothermal amplification technologies, they both have adopted a fluorescent labeling method for real-time detection at present. Fluorescence detection requires fluorescent markers to be added in, but the addition of the fluorescent markers would affect biological reactivity and result in problems such as fluorescence attenuation, quenching, and instability. Moreover, in the case that some reagents in biological reactions react with the fluorescent markers, the fluorescent labeling method cannot be adopted for detection. In the fluorescence detection, tubes of a 96-well plate or 384-well plate serve as carriers, and each index analysis requires a reagent of 25 μL reaction volume, which is not applicable for those biological reactions having a relatively small sample volume. An actual sensitivity of the fluorescence detection is more than $10^3$ nucleic acid copy numbers, but an instrument used therefore is expensive, consumption of sample reagents is large, and the cost for the detection is high. Thus, it is not applicable to low-cost precision medical analysis and detection with collection of multiple indexes. In addition, there are also a small number of nucleic acid amplification instruments that use a turbidity measurement method for detection, but their detection sensitivity is not high, and detection results thereof are not as accurate as a fluorescence detector. As a result, they can only be used in an occasion where high experimental accuracy is not required, such as final qualitative analysis.

SUMMARY OF THE INVENTION

Because of the above-mentioned shortcomings of the existing technologies, the objective of the present disclosure is to provide a nucleic acid amplification in-situ real-time detection system and method using a microfluidic chip through optical fiber sensing, in which a white light interfered hyperspectral method is used to detect nucleic acid amplification information so as to detect a non-fluorescence-labeled analyte. In this way, the problems such as biological reaction activity being affected by a fluorescence-labeled detection method as well as fluorescence attenuation, quenching and instability can be solved very well.

To achieve the above objective, the present disclosure provides a nucleic acid amplification in-situ real-time detection system using a microfluidic chip through optical fiber sensing, including: one or more white light sources, one or more first optical fiber sensors, one or more detection optical paths, one or more microfluidic chips, a multi-path PID temperature control system, a CAN-bus multi-axis motion control system, one or more second optical fiber sensors, and a spectrum acquisition, processing and display module; each of the white light sources is configured to generate white light; the first optical fiber sensors connect a white light source and a detection optical path; the detection optical paths is configured to transmit the white light generated by the white light source to a microfluidic chip, and then transmit an optical signal passing through the microfluidic chip to the spectrum acquisition, processing and display module; each of the microfluidic chips is configured to carry out biochemical reaction, and a sample to be detected in the microfluidic chip is subjected to no fluorescence-labeling; the microfluidic chip is further connected to a temperature controller, the multi-path PID temperature control system is configured to regulate a temperature of the microfluidic chip, and the multi-path PID temperature control system is connected to the CAN-bus multi-axis motion control system; the second optical fiber sensors are configured to transmit the optical signal of the microfluidic chip to the spectrum acquisition, processing and display module; the spectrum acquisition, processing and display module includes an optical fiber scanner that receives the optical signal transmitted by the second optical fiber sensors; the spectrum acquisition, processing and display module analyzes the optical signal, and generates visualized biochemical reaction real-time dynamic change signal curves.

Further, the detection optical path performs white light interfered hyperspectral non-label real-time detection for a trace sample placed inside a reaction unit of the microfluidic chip, and sends a detection result to the spectrum acquisition, processing and display module in real time; the optical fiber scanner controls a plurality of the optical fiber sensors in a rotational or translational scanning manner, so that white light interfered hyperspectral signals received from a plurality of the detection optical paths are transmitted to the spectrum acquisition, processing and display module one by one so as to enable high-throughput parallel nucleic acid amplification non-label in-suit real-time detections by a plurality of the microfluidic chips through optical fiber sensing.

Further, the microfluidic chip is arranged inside a thermostatic airtight cavity which is provided inside with a heater, a temperature sensor, and a temperature controller; the heater is arranged at the upper and lower surfaces of the microfluidic chip, and heats the microfluidic chip through a flowing heating method using a sub-millimeter thin-layer air bath; the temperature controller is configured to control the temperature of the microfluidic chip; opening/closing of the thermostatic airtight cavity is controlled by the CAN-bus multi-axis motion control system to facilitate loading/unloading of the microfluidic chip.

Further, the center of the microfluidic chip is in shaft connection with a first motor, and the CAN-bus multi-axis motion control system controls the rotation of the first motor to drive the microfluidic chip to rotate, so that uniformity of the temperature in the thermostatic airtight cavity is ensured, driving of a fluid switching control unit on the microfluidic chip is implemented, and the need for step-by-step control of sample preparation, nucleic acid or protein sample separation and purification, and nucleic acid amplification is met.

Further, the microfluidic chip includes a liquid storage unit, a micro-fluid switching control unit, a sample inlet, a nucleic acid extraction unit, amplification reaction chamber units, buffer and adjustment units, and a waste liquid storage unit, which are connected in sequence; the liquid storage unit, the micro-fluid switching control unit, the reaction chamber units and the waste liquid storage unit are connected through a micro-fluid channel.

Further, a silicon-based $SiO_2$ layer microchip is fixed at the bottom of an amplification reaction chamber unit, and the silicon-based $SiO_2$ layer microchip is modified with a gripper probe for nucleic acid or protein molecules. The gripper probe can bio-specifically bind a nucleic acid amplification product in the solution to a surface of the microchip, or allow the nucleic acid amplification product to continually bio-specifically extend on the surface of the microchip over time to form a long chain. Alternatively, specific amplification primers embedded in a low-melting agarose gel are provided at the bottom of the amplification reaction chamber unit, which are released after heating to perform nucleic acid amplification and produce a nucleic acid amplification product. The nucleic acid amplification product binds to fluorescent molecules to enable dynamic characterization concerning the amplification reaction process in the microfluidic chip.

Furthermore, the detection system includes several detection modes, among which a multi-path white light/fluorescence switching control system is provided for switching of the detection modes. One of the detection modes is a white light interfered hyperspectral non-labeled in-situ detection mode, in which a detection optical path includes an interface connected to the white light source, a condenser, a beam splitter, a reflector and an objective lens, which are coupled in sequence. The white light enters the detection optical path via the interface, and then reaches the microfluidic chip after being subjected to transmission by the condenser and the beam splitter, reflection by the reflector, and focus by the objective lens; a reflected light signal generated by the microfluidic chip is subjected to the objective lens, the reflection of the reflector, the reflection of the beam splitter, and transmission of an imaging lens, and then passes through an optical shutter and reaches the spectrum acquisition, processing and display module. Alternatively, in the detection optical path, a plurality of second optical fiber sensors may be arranged into a linear array and directly coupled into an area array spectrometer detector, and the optical shutter of the detection optical path is controlled by the multi-path white light/fluorescence switching control system, so as to enable the white light interfered hyperspectral non-labeled in-situ detection to be applied on the microfluidic chip.

Further, another of the detection modes is a fluorescence detection mode, in which by using the multi-path white light/fluorescence switching control system, a first filter is arranged between the condenser and the beam splitter, and a second filter is arranged between the beam splitter and the imaging lens.

Further, the multi-path white light/fluorescence switching control system includes a second motor or electromagnet which is configured to control positions and states of the first filter, the second filter and the optical shutter, thereby enabling switching among white light interfered hyperspectral detection, fluorescence detection and Raman spectroscopy detection. Alternatively, it is possible that a plurality of second optical fiber sensors are arranged into an area array and directly coupled into an area array CCD detector, a photomultiplier tube or other photoelectric detectors, or that the area array arranged with the plurality of second optical fiber sensors are imaged onto an area array CCD detector or a photomultiplier tube by using a lens or a set of lenses, so as to enable the fluorescence signal detection or the Raman spectroscopy detection to be applied to the microfluidic chip.

The present disclosure further discloses a nucleic acid amplification in-situ real-time detection method using a microfluidic chip through optical fiber sensing, including steps of: S1, fixing, according to specificity of nucleic acid to be detected, the gripper probe for nucleic acid detection on the silicon-based $SiO_2$ layer microchip arranged at the bottom of a reaction channel of the microfluidic chip; S2, injecting, step by step in sequence, an original sample to be analyzed and reaction reagents into corresponding micro-fluid channels of the microfluidic chip via the sample inlet, and then placing them into the above-mentioned nucleic acid amplification in-situ real-time detection system using a microfluidic chip through optical fiber sensing; S3, opening, by the CAN-bus multi-axis motion control system, the thermostatic airtight cavity, installing the microfluidic chip onto an output shaft of the first motor, and closing the thermostatic airtight cavity; in the thermostatic airtight cavity, the first motor drives rotation of the microfluidic chip to drive the micro-fluid switching control unit of the microfluidic chip, so as to complete a fluid control process of a series of biochemical reactions, such as sample preparation, nucleic acid or protein sample separation and purification, and nucleic acid amplification; S4, detecting, by the detection optical path, a product of the nucleic acid amplification process in the microfluidic chip, and sending, in real time, a detection result to the spectrum data acquisition and processing display module, then decoding, by the spectrum data acquisition and processing display module in real time, a hyperspectral signal interfered by the reflected light and the incident light of the microfluidic chip to form visualized nucleic acid amplification non-labeled in-situ measurement real-time dynamic change signal curves; S5, controlling, by the second motor or electromagnet, positions and states of the first filter, the second filter and the optical shutter, and switching a detection mode to the fluorescence detection mode or the Raman spectroscopy detection mode for measurement; S6, configuring the spectrum acquisition, processing and display module that includes a white light interfered nucleic acid amplification non-labeled in-situ real-time detection and analysis algorithm software to decode the white light interfered hyperspectral signal in real time to form visualized nucleic acid amplification real-time dynamic change signal curves; the white light interfered nucleic acid amplification non-labeled in-situ real-time detection and analysis algorithm software applies extraction and decoding of specific wavelength fluorescence or of Raman spectrum on the white light interfered hyperspectral signal, so as to form the visualized real-time dynamic change curves of the nucleic acid amplification fluorescence signal or the Raman spectrum.

The present disclosure has the following advantages by adopting the foregoing technical solutions: 1. The white light interfered hyperspectral method is used herein to detect nucleic acid amplification information, so that both fluorescence-labeled analyte and non-fluorescence-labeled analyte can be detected, and not only the accuracy of fluorescence detection can be ensured, but also problems such as biological reaction activity being affected by a fluorescence-labeled detection method as well as fluorescence attenuation, quenching and instability can be solved very well. 2. Optical fiber sensors are used herein to transmit optical signals, switching among the optical signals of various detection optical paths is performed by the optical shutter, and one same spectrum acquisition, processing and display module is used, so that high-throughput detections of a plurality of fully integrated microfluidic chips are achieved, which can meet daily practical application demands of high-throughput nucleic acid amplification detection of dozens to 200 samples. 3. The microfluidic chip used herein can not only complete a series of biochemical reaction processes such as sample preparation, nucleic acid or protein sample separation and purification, and nucleic acid amplification under a fully enclosed environment, but also achieve parallel detection identifications of a collection of multiple nucleic acid analysis indexes at one time, in which a sample-reagent mixed reaction volume of a single index detection is ≤1.0 μL, detection sensitivity is up to 10 copy numbers of nucleic acid molecules, and the microfluidic chip is heated through a flowing heating method using a sub-millimeter thin-layer air bath, so that the heating speed is fast and the temperature field is uniform, thereby ensuring good temperature consistency among multiple reaction channels on the microfluidic chip. 4. The device herein includes a white light interfered hyperspectral mode, a fluorescence measurement mode and a Raman spectroscopy mode, switching among the respective modes is enabled to meet the needs of different detection applications. 5. The microfluidic chip herein is compatible with various nucleic acid extraction methods, such as mechanical lysis, high-voltage electrical pulse lysis, chemical reagent lysis, etc., and is suitable for various sample forms, such as original samples, intermediate samples after certain pretreatment, and nucleic acid/protein after separation and purification, thereby meeting the practical application needs of low-cost precision medical molecular diagnosis in the fields of scientific research, clinical medicine, food safety, and sanitation and epidemic prevention.

BRIEF DESCRIPTION OF THE DRAWINGS

FIG. 1 is a schematic diagram showing the structure of a microfluidic chip real-time detection device according to an embodiment of the present disclosure;

FIGS. 2(A)-2(D) is a schematic diagram showing the structure of a microfluidic chip according to an embodiment of the present disclosure, in which 2(A) is a schematic diagram of the structure of a cover sheet of the microfluidic chip; 2(B) is a schematic diagram of the structure of a base of the microfluidic chip; 2(C) is a schematic diagram of the structure of a micro-fluid switching control unit; 2(D) is a schematic diagram of the structure of a silicon-based $SiO_2$ layer microchip;

FIGS. 3(A)-3(C) shows 3(A) which is a schematic diagram of the principle of white light interference according to the present disclosure, 3(B) which is a spectrogram of hyperspectral digital signals of a microfluidic chip, 3C which is dynamic change signal curves of the microfluidic chip; and FIGS. 4(A)4(D) is a schematic diagram showing steps of a detection method of inserting fluorescence into specific amplification primers embedded in low-melting agarose gel which are released after heating according to an embodiment of the present disclosure.

LIST OF THE REFERENCE NUMBER

1—White light source; 2—Detection optical path; 21 and 210—Interface; 22—Condenser; 23—Beam splitter; 24—Reflector; 25—Objective lens; 26—Imaging lens; 27—Optical shutter; 28—First filter; 29—Second filter; 3—Microfluidic chip; 31—Liquid storage unit; 32—Micro-fluid switching control unit; 33—Sample inlet; 34—Reaction chamber unit; 341—Nucleic acid extraction unit; 342—Amplification reaction chamber unit; 343—Buffer and adjustment unit; 35—Waste liquid storage unit; 36—Micro-fluid channel; 37—Multi-path PID temperature control system; 38—Heater; 39—Silicon-based $SiO_2$ layer microchip; 391—Gripper probe; 392—Amplified product; 4—Spectrum acquisition, processing and display module; 41—Fiber scanner; 42—Photoelectric converter; 43—Display; 51—First optical fiber sensor; 52—Second optical fiber sensor; 6—CAN-bus multi-axis motion control system; 7—First motor; 8—Multi-path white light/fluorescence switching control system.

DETAILED DESCRIPTION OF THE EMBODIMENTS

Hereinafter, the present disclosure will be described in detail regarding the accompanying drawings. However, it should be understood that the drawings are only provided for a better understanding of the present disclosure, and should not be considered as a limitation to the present disclosure. In the description of the present disclosure, it should be understood that terms used herein are only for descriptive purposes, and cannot be considered as indications or implications of relative importance.

The present embodiment provides a nucleic acid amplification in-situ real-time detection system using a microfluidic chip 3 through optical fiber sensing, as shown in FIG. 1, which includes: a white light source 1, detection optical paths 2, microfluidic chips 3, and spectrum acquisition, processing and display module 4, a multi-path proportion-integration-differentiation (PID) temperature control system 37, a CAN-bus multi-axis motion control system 6, a multi-path white light/fluorescence switching control system 8, which are connected in sequence. The white light source 1 is configured to generate white light for experiment; each of the detection optical paths 2 is configured to transmit the white light generated by the white light source 1 to a microfluidic chip 3, and then transmit an optical signal made by the microfluidic chip 3 to the spectrum acquisition, processing and display module 4; each of the microfluidic chips 3 is configured to carry out biochemical reaction; the spectrum acquisition, processing and display module 4 is configured to acquire optical signals passing through the microfluidic chips 3, analyze the optical signals, and generate visualized biochemical reaction real-time dynamic change signal curves; the CAN-bus multi-axis motion control system is configured to drive and control movement of each microfluidic chip; the multi-path PID temperature control system is configured to adjust and control a temperature of each microfluidic chip; and the multi-path white light/fluorescence switching control system 8 is configured to control positions of an excitation filter 28, an emission filter 29, and an optical shutter 27 in each detection optical path 2 through an electromagnet expansion or motor stepping manner, so as to enable automatic switching among a white light interfered hyperspectral non-labeled in-situ measurement, an excitation light induced emission fluorescence measurement, and a Raman spectroscopy detection. This microfluidic chip real-time detection device detects nucleic acid amplification information by using a white light interfered hyperspectral method, so that both fluorescence-labeled analyte and non-fluorescence-labeled analyte can be detected, and not only the accuracy of fluorescence detection can be ensured, but also problems such as biological reaction activity being affected by a fluorescence-labeled detection method as well as fluorescence attenuation, quenching and instability can be solved thereby.

In this case, there may be one or more white light sources 1. When there is a plurality of microfluidic chips 3, it is possible to use only one white light source 1, which is connected to respective detection optical paths 2 through first optical fiber sensors 51. Alternatively, it is possible that each of the detection optical paths 2 is provided with a corresponding white light source 1, which is directly connected to the detection optical path 2. The white light source 1 may be a white light LED lamp, a halogen tungsten lamp or other light sources.

The device in the present embodiment has three modes, that is, a white light interfered hyperspectral mode, a fluorescence measurement mode, and a Raman spectrum mode. The various modes are switched by the multi-path white light/fluorescence switching control system 8. This mode switching module implements the switching of the three modes by adjusting optical elements and their positions in the detection optical path 2. A specific process thereof is as follows.

In the case of the white light interfered hyperspectral mode, a detection optical path 2 includes an interface 21 connected to the white light source 1, a condenser 22, a beam splitter 23, a reflector 24, and an objective lens 25, which are coupled in sequence. The white light enters the detection optical path 2 via interface 21, and then reaches the microfluidic chip 3 after being subjected to condensation by the condenser 22, transmission by the beam splitter 23, reflection by the reflector 24, and focus by the objective lens 25. A hyperspectral signal generated by interfering the reflected light generated by the microfluidic chip 3 with the incident light is subjected to the objective lens 25, the reflection of the reflector 24, the reflection of the beam splitter 23, and transmission of an imaging lens 26, and then passes through an optical shutter 27 and reaches the spectrum acquisition, processing and display module 4. Alternatively, in the detection optical path 2, it is possible that a plurality of second optical fiber sensors 52 are arranged into a linear array and directly coupled into an area array spectrometer detector 42, and the optical shutter of the detection optical path 2 is controlled by the multi-path white light/fluorescence switching control system 8, so as to enable white light interfered hyperspectral non-labeled in-situ detection to be applied on the microfluidic chip 3.

In the case of the fluorescence detection mode, based on the detection optical path 2 configured for the white light interfered hyperspectral mode, the detection optical path 2 further includes a first filter 28 arranged between the condenser 22 and the beam splitter 23, and a second filter 29 arranged between the beam splitter 23 and the imaging lens 26.

In the case of the Raman detection mode, the detection optical path 2 is generally the same as the detection optical path 2 configured for the fluorescence detection mode, except that wavelength ranges of the first filter 28 and the second filter 29 are different from that of the fluorescence detection mode. Besides, detection time and processing of data in the spectrum acquisition, processing and display module 4 are also different from that of the fluorescence detection mode.

In the present embodiment, the device further includes one or more first optical fiber sensors 51 and second optical fiber sensor 52. The first optical fiber sensors 51 are configured to guide the white light emitted by the white light source 1 into the detection optical path 2. The second optical fiber sensor 52 is configured to transmit an optical signal generated in the detection optical path 2 to the spectrum acquisition, processing and display module 4. The spectrum acquisition, processing and display module 4 include a multi-fiber scanner 41, which acquires optical signals in one or more detection optical paths 2 in a rotational or translational scanning manner and transmits the acquired optical signal(s) to the photoelectric converter 42. The optical signals are analyzed by a white light interfered nucleic acid amplification non-labeled in-situ real-time detection and analysis algorithm software included in the spectrum acquisition, processing and display module 4, and are visually displayed by a display 43 of the spectrum acquisition, processing and display module 4. The photoelectric converter 42 may be a charge-coupled-device (CCD) detector, a photomultiplier tube or other photodetectors. Alternatively, it is possible that a plurality of second optical fiber sensors are arranged into an area array and directly coupled into the area array CCD detector, the photomultiplier tube or other photoelectric detectors, or that the area array arranged with the plurality of second optical fiber sensors are imaged onto the area array CCD detector, the photomultiplier tube or other photodetectors by using a lens or a set of lenses, so as to enable the fluorescence signal detection or the Raman spectroscopy detection to be applied to the microfluidic chip.

In the case that there is a plurality of detection optical paths 2, the second optical fiber sensors 52 may be arranged into an array, where a whole of the said array may be a one-dimensional array, i.e., it has only one row or one column. The array of the second optical fiber sensors 52 may be directly coupled into an area array spectrum detector, or the second optical fiber sensors 52 may be provided with an optical shutter 27 by mean of which optical signals of the detection optical paths 2 can be received in a selectable manner, that is, it can be determined whether to receive an optical signal of a specific detection optical path 2 or not.

In this case, mode switching modules include the multi-path white light/fluorescence switching control system 8, the optical shutter 27, and a second motor or electromagnet that controls positions of the above-mentioned first filter 28 and the second filter 29, an on/off state of the optical shutter 27, and wavelength ranges of the first and second filters. Preferably, there are a plurality of motors and electromagnets. Herein, "a plurality of" refers to two or more. The second motor or electromagnet implements switching among the various modules of the device by controlling the optical shutter 27, the first filter and the second filter.

As shown in FIGS. 2 (A) to 2(D), the microfluidic chip 3 is enclosed by a cover sheet (as shown in FIG. 2 (A)) and a base (as shown in FIG. 2 (B)). The microfluidic chip 3 includes a liquid storage unit 31, a micro-fluid switching control unit 32, a sample inlet 33, 24 reaction chamber units 342, 24 buffer chamber units 343, and a waste liquid storage unit 35, which are connected in sequence. The liquid storage unit 31, the micro-fluid switching control unit 32, the reaction chamber units 342, the buffer chamber units 343 and the waste liquid storage unit 35 are connected through a micro-fluid channel 36. The sample inlet 33 of the micro-fluidic chip 3 adopts a silicone rubber structure and is communicated with the liquid storage unit 31 for various original samples or reaction reagents via the micro-fluid channel 36. The sample inlet 33 is suitable for sample injection through a needle or other rubber-piercing injectors, and can be self-sealed automatically upon withdrawn of the needle after the sample injection so that the sample injection can be repeated multiple times. A center of the microfluidic chip 3 is in shaft connection with a first motor 7, and the first motor 7, driven by the CAN-bus multi-axis motion control system 6, drives the microfluidic chip 3 to rotate so as to enable switching of the micro-fluids. Besides, a rotation rate of the motor is controlled by the CAN-bus multi-axis motion control system 6 so as to enable centrifugation to be applied on the liquid in the microfluidic chip 3. Since a routine biochemical experiment requires centrifugation to be applied on the sample multiple times, if a centrifuge was set up separately, then not only would complicated operations and a high cost be resulted, but also sample waste and pollution be caused easily. In this embodiment, a centrifuge unit is united with the micro-fluid switching control unit 32, which is reasonable in design and simplifies the experiment process. As shown in FIG. 2(C), through centrifugal drive by the first motor 7, step-by-step control of the micro-fluid switching control unit in the microfluidic chip 3 is enabled, so that the liquids inside the microfluidic chip 3 perform step-by-step directional flowing according to the biochemical reaction process in a closed environment. In this embodiment, the microfluidic chip 3 is compatible with various forms of samples, such as original samples such as blood, sputum, saliva, stool and urine, and tissue cells, or intermediate samples subjected to certain pre-processing, or nucleic acid/protein samples after separation and purification, and it therefore has a wide application range and strong operability.

The microfluidic chip 3 in the present embodiment is arranged inside a thermostatic airtight cavity. The thermostatic airtight cavity is provided inside with a heater 38, temperature sensors, and a multi-path PID temperature control system 37, which are connected in sequence. The multi-path PID temperature control system 37 is configured to adjust and control the temperature of the microfluidic chip 3. The heater 38 includes more than one heating film which has a one-to-one correspondence with the temperature sensors. However, it is also possible to provide only one temperature sensor for detecting the thermostatic airtight cavity. The heating films adopt an upper and lower two-piece structure and form the thermostatic airtight cavity together with metal heat exchange layers, and are wrapped outside with a heat preservation and insulation material. The heating films are located on upper and lower surfaces of the microfluidic chip 3 to form a sub-millimeter air layer, so as to perform rapid, uniform and three-dimensional heating of the microfluidic chip 3. The CAN-bus multi-axis motion control system 6 controls the opening/closing of the thermostatic airtight cavity to load/unload the microfluidic chip 3. The CAN-bus multi-axis motion control system 6 controls rotation of the first motor 7 to drive the microfluidic chip to rotate, so that uniformity of the temperature in the thermostatic airtight cavity can be further ensured.

The microfluidic chip 3 real-time detection device in the present embodiment can be used for nucleic acid amplification reactions. When it is used for nucleic acid amplification reactions, a reaction chamber unit 34 includes a nucleic acid extraction unit 341, amplification reaction chamber units 342, and buffer and adjustment units 343. The nucleic acid extraction unit 341 of the microfluidic chip 3 in this embodiment is compatible with various nucleic acid extraction approaches, such as mechanical lysis, high-voltage electric pulse lysis, and chemical reagent lysis.

As shown in FIG. 2(D), the bottom of an amplification reaction chamber unit 342 is fixedly provided with a silicon-based $SiO_2$ layer microchip 39, on which a nucleic acid or protein molecule gripper probe 391 is modified thereon. The gripper probe 391 can bio-specifically bind a nucleic acid amplification product 392 in the solution to a surface of the microchip, or allow the nucleic acid amplification product 392 to continually bio-specifically extend on the surface of the microchip over time to form a long chain. The shape of the $SiO_2$ layer microchip is preferably square or circular.

As shown in FIGS. 3(A)-3(C), FIG. 3(A) is a schematic diagram showing the principle of white light interference. A $SiO_2$ layer of hundreds of nanometers is vacuum-coated on a single-crystal Si wafer. The $SiO_2$ layer is fixedly modified with the gripper probe 391. The white light illuminates the $SiO_2$ layer, a reflected light that is reflected from the gripper probe 391 is RL1, and a reflected light that is reflected from the gripper probe 391 together with the amplification product 392 is RL2. A white light interfered hyperspectral signal superimposed by the incident light of the $SiO_2$ layer and the reflected light RL1 and RL2 is acquired and transmitted to the spectrum acquisition, processing and display module to generate hyperspectral digital signals, including an interference curve corresponding to the $SiO_2$ layer, an interference curve corresponding to the gripper probe 391, and an interference curve corresponding to the amplification product 392, as shown in FIG. 3(B). Finally, real-time analysis is performed by using the white light interfered nucleic acid amplification non-labeled in-situ real-time detection and analysis algorithm software to form visualized nucleic acid amplification non-labeled in-situ detection real-time dynamic change signal curves (i.e., Positive Sample and Negative Sample), as shown in FIG. 3(C).

In another embodiment, nucleic acid amplification can also be implemented by using specific amplification primers embedded in low-melting agarose gel. The specific amplification primers are released after heating, and then perform nucleic acid amplification to generate a nucleic acid amplification product. Then, an amplification reaction process in the microfluidic chip is dynamically characterized by binding the nucleic acid amplification product binds to fluorescent molecules. The specific process is shown in FIG. 4(A) to FIG. 4(D). As shown in FIG. 4(A) and FIG. 4(B), low-melting agarose gel is provided at the bottom of the amplification reaction chamber unit 342 of the microfluidic chip 3, specific amplification primers are embedded in the low-melting agarose gel and released after heating to perform nucleic acid amplification and produce a nucleic acid amplification product, and the nucleic acid amplification product binds to fluorescent molecules to characterize the amplification reaction process in the microfluidic chip 3. As shown in FIG. 4(C), after the sample and reagents are added, they are placed into a detection optical path 2, and the samples and reagents are automatically mixed and evenly distributed into the 24 amplification reaction chamber units 342 through a centrifugal operation. Subsequently, the microfluidic chip 3 is heated to above 40° C., and the specific amplification primers embedded in the low-melting agarose gel are heated and released then. As shown in FIG. 4(D), the microfluidic chip 3 is then heated to above 60° C., the specific amplification primers released in the previous step will continuously perform replication of specific nucleic acid fragments under the action of polymerase in accordance with the principle of nucleic acid amplification and also perform simultaneous binding with the fluorescent labeling molecules to emit fluorescence under the induction of excitation light. Finally, the spectrum acquisition, processing and display module 4 perform real-time decoding to form visualized signal dynamic change curves of the nucleic acid amplification real-time fluorescent signal detection.

Although the present embodiment is described by taking nucleic acid amplification reaction as an example, those skilled in the art should understand that the device in this embodiment can also be used for other biochemical experiments that require optical detection, especially for those experiments with more complicated processes.

Taking the nucleic acid amplification reaction as an example, the device in the present embodiment includes the following steps S1 to S6.

S1, According to the specificity of nucleic acid to be detected, the gripper probe for nucleic acid detection is fixed on the silicon-based $SiO_2$ layer microchip arranged at the bottom of a reaction channel of the microfluidic chip;

S2, An original sample to be analyzed and reaction reagents are injected, step by step in sequence, into corresponding micro-fluid channels of the microfluidic chip via the sample inlet, and then placed into any one of the above-mentioned nucleic acid amplification in-situ real-time detection systems of the microfluidic chip through optical fiber sensing;

S3, The thermostatic airtight cavity is opened by the CAN-bus multi-axis motion control system, and the microfluidic chip is installed onto an output shaft of the first motor, and then the thermostatic airtight cavity is closed; in the thermostatic airtight cavity, the first motor drives rotation of the microfluidic chip to drive the micro-fluid switching control unit of the microfluidic chip, so as to complete fluid control processes, such as sample preparation, nucleic acid or protein sample separation and purification, and nucleic acid amplification;

S4, A product of the nucleic acid amplification process in the microfluidic chip is detected by the detection optical path, and a detection result is sent, in real time, to the spectrum data acquisition and processing display module, then the spectrum data acquisition and processing display module decodes, in real time, a hyperspectral signal interfered by the reflected light and the incident light of the microfluidic chip to form visualized nucleic acid amplification non-labeled in-situ measurement real-time dynamic change signal curves;

S5, Positions and states of the first filter, the second filter and the optical shutter are controlled by the second motor or electromagnet, so that the detection mode is switched to the fluorescence detection mode or the Raman spectroscopy detection mode for measurement;

S6, The spectrum acquisition, processing and display module including a white light interfered nucleic acid amplification non-labeled in-situ real-time detection and analysis algorithm software is configured to decode the white light interfered hyperspectral signal in real time to form visualized nucleic acid amplification real-time dynamic change signal curves; the white light interfered nucleic acid amplification non-labeled in-situ real-time detection and analysis algorithm software applies extraction and decoding of specific wavelength fluorescence or of Raman spectrum on the white light interfered hyperspectral signal, so as to form the visualized real-time dynamic change curves of the nucleic acid amplification fluorescence signal or the Raman spectrum.

The foregoing embodiments are only used to illustrate the present disclosure. The structure, size, installation position and shape of each component can be changed, such as an appearance size, a fixing manner, a wiring manner, and a geometric structure after assembly of each component. On the basis of the technical solution of the present disclosure, any improvement and equivalent replacement made to an individual component based on the principle of the present disclosure should not be excluded from the protection scope of the present disclosure.

The invention claimed is:

1. A nucleic acid amplification in-situ real-time detection system using a microfluidic chip through optical fiber sensing, wherein, the system comprises: one or more white light sources, one or more first optical fiber sensors, one or more detection optical paths, one or more microfluidic chips, a multi-path PID temperature control system, a CAN-bus multi-axis motion control system, one or more second optical fiber sensors, and a spectrum acquisition, processing and display module;

wherein each of the white light sources is configured to generate white light;

the first optical fiber sensors connect a white light source and a detection optical path;

the detection optical path is configured to transmit the white light generated by the white light source to a microfluidic chip and then transmit an optical signal made by the microfluidic chip to the spectrum acquisition, processing and display module;

the microfluidic chip is configured to carry out biochemical reaction, and a sample to be detected in the microfluidic chip is subjected to no fluorescence-labeling; the microfluidic chip is further connected to a temperature controller, the multi-path PID temperature control system is configured to regulate a temperature of the microfluidic chip, and the multi-path PID temperature control system is connected to the CAN-bus multi-axis motion control system;

the second optical fiber sensors are configured to transmit the optical signal of the microfluidic chip to the spectrum acquisition, processing and display module; and the spectrum acquisition, processing and display module includes an optical fiber scanner for receiving the optical signal transmitted by the second optical fiber sensors; the spectrum acquisition, processing and display module analyzes the optical signal and generates visualized biochemical reaction real-time dynamic change signal curves;

wherein, the microfluidic chip comprises a liquid storage unit, a micro-fluid switching control unit, a sample inlet, a nucleic acid extraction unit, amplification reaction chamber units, buffer and adjustment units, and a waste liquid storage unit, which are connected in sequence, wherein the liquid storage unit, the micro-fluid switching control unit, the reaction chamber units and the waste liquid storage unit are connected with each other through a micro-fluid channel.

2. The nucleic acid amplification in-situ real-time detection system using a microfluidic chip through optical fiber sensing according to claim 1, wherein, the detection optical path performs white light interfered hyperspectral non-label real-time detection for a trace sample placed within a reaction unit of the microfluidic chip, and sends a detection result to the spectrum acquisition, processing and display module in real time; the optical fiber scanner controls a plurality of the optical fiber sensors in a rotational or translational scanning manner so that white light interfered hyperspectral signals received from a plurality of the detection optical paths are transmitted to the spectrum acquisition, processing and display module one by one, so as to enable high-throughput parallel nucleic acid amplification non-label in-suit real-time detections by a plurality of the microfluidic chips through optical fiber sensing.

3. The nucleic acid amplification in-situ real-time detection system using a microfluidic chip through optical fiber sensing according to claim 1, wherein, the microfluidic chip is arranged inside a thermostatic airtight cavity which is provided inside with a heater, a temperature sensor, and a temperature controller, wherein the heater is arranged at upper and lower surfaces of the microfluidic chip and heats the microfluidic chip though a flowing heating method using a sub-millimeter thin-layer air bath; the temperature controller is configured to control the temperature of the microfluidic chip; opening/closing of the thermostatic airtight cavity is controlled by the CAN-bus multi-axis motion control system to facilitate loading/unloading of the microfluidic chip.

4. The nucleic acid amplification in-situ real-time detection system using a microfluidic chip through optical fiber sensing according to claim 3, wherein, a center of the microfluidic chip is in shaft connection with a first motor, and the CAN-bus multi-axis motion control system controls rotation of the first motor to drive the microfluidic chip to rotate, so that uniformity of temperature in the thermostatic airtight cavity is ensured, driving of a fluid switching control unit on the microfluidic chip is implemented, and a need for step-by-step control of sample preparation, nucleic acid or protein sample separation and purification, and nucleic acid amplification is met.

5. The nucleic acid amplification in-situ real-time detection system using a microfluidic chip through optical fiber sensing according to claim 1, wherein, a silicon-based $SiO_2$ layer microchip is fixed at a bottom of an amplification reaction chamber unit, and the silicon-based $SiO_2$ layer microchip is modified with a gripper probe for nucleic acid or protein molecules, wherein the gripper probe can biospecifically bind a nucleic acid amplification product in solution to a surface of the microchip, or allow the nucleic acid amplification product to continually biospecifically extend on the surface of the microchip over time to form a long chain; or specific amplification primers embedded in a low-melting agarose gel are provided at the bottom of the amplification reaction chamber unit, which are released after heating to perform nucleic acid amplification and produce a nucleic acid amplification product, the nucleic acid amplification product binds to fluorescent molecules to enable dynamic characterization with respect to the amplification reaction process in the microfluidic chip.

6. The nucleic acid amplification in-situ real-time detection system using a microfluidic chip through optical fiber sensing according to claim 1, wherein, the detection system includes a number of detection modes, among which a multi-path white light/fluorescence switching control system is provided for switching of the detection modes, wherein one of the detection modes is a white light interfered hyperspectral non-labeled in-situ detection mode, in which a detection optical path includes an interface connected to the white light source, a condenser, a beam splitter, a reflector and an objective lens, which are coupled in sequence; the white light enters the detection optical path via the interface and then reaches the microfluidic chip after being subjected to transmission by the condenser and the beam splitter, reflection by the reflector, and focus by the objective lens; a reflected light signal generated by the microfluidic chip is subjected to the objective lens, reflection of the reflector, reflection of the beam splitter, and transmission of an imaging lens, and then passes through an optical shutter and reaches the spectrum acquisition, processing and display module; or a plurality of second optical fiber sensors are arranged into a linear array in the detection optical path and directly coupled into an area array spectrometer detector, and an optical shutter of the detection optical path is controlled by a multi-path white light/fluorescence switching control system, so as to enable the white light interfered hyperspectral non-labeled in-situ detection to be applied on the microfluidic chip.

7. The nucleic acid amplification in-situ real-time detection system using a microfluidic chip through optical fiber sensing according to claim 6, wherein, another of the detection modes is a fluorescence detection mode, in which by using the multi-path white light/fluorescence switching control system, a first filter is arranged between the condenser and the beam splitter, and a second filter is arranged between the beam splitter and the imaging lens.

8. The nucleic acid amplification in-situ real-time detection system using a microfluidic chip through optical fiber sensing according to claim 7, wherein, the multi-path white light/fluorescence switching control system includes a second motor or electromagnet which is configured to control positions and states of the first filter, the second filter and the optical shutter, thereby enabling switching among white light interfered hyperspectral detection, fluorescence detection and Raman spectroscopy detection, or a plurality of second optical fiber sensors are arranged into an area array and directly coupled into an area array CCD detector, a photomultiplier tube or other photoelectric detectors, or the area array arranged with the plurality of second optical fiber sensors are imaged onto an area array CCD detector or a photomultiplier tube by using a lens or a set of lenses, so as to enable the fluorescence signal detection or the Raman spectroscopy detection to be applied to the microfluidic chip.

* * * * *